United States Patent [19]

Poetsch et al.

[11] Patent Number: 5,639,883

[45] Date of Patent: Jun. 17, 1997

[54] PROCESS FOR PREPARING SUBSTITUTED 4-METHYLIDENECINNAMIC ACID DERIVATIVES

[75] Inventors: Eike Poetsch, Muhltal; Volker Meyer, Gross-Zimmern; Ulrich Heywang, Darmstadt; Inge Stein, Erzhausen; Michael Schwarz, Bross-Gerau; Michael Kompter, Riedstadt, all of Germany

[73] Assignee: Merck Patent Gesellschaft Mit Beschrankter Haftung, Darmstadt, Germany

[21] Appl. No.: 487,093

[22] Filed: Jun. 6, 1995

[30] Foreign Application Priority Data

Jul. 12, 1994 [DE] Germany ............ 44 24 489.4

[51] Int. Cl.⁶ ........................... C07D 453/02
[52] U.S. Cl. ............... 546/137; 568/367; 568/373
[58] Field of Search ............ 546/137; 568/367, 568/373

[56] References Cited

U.S. PATENT DOCUMENTS

| | | |
|---|---|---|
| 3,560,510 | 2/1971 | Warawa . |
| 4,564,479 | 1/1986 | Spencer . |
| 4,710,584 | 12/1987 | Lang et al. . |

FOREIGN PATENT DOCUMENTS

| | | |
|---|---|---|
| 103544 | 9/1983 | European Pat. Off. . |
| 2556592 | 6/1985 | France . |
| 4204922 | 8/1993 | Germany . |
| 2121801 | 1/1984 | United Kingdom . |

OTHER PUBLICATIONS

Warawa et al., "Quinuclidine Chemistry.1.¹β-cis-2-(4'-Chlorobenzhydryl) J. Med. Chem., "1975, vol. 18. No. 1 pp. 71-74.

Warawa et al., "Quinuclidine Chenustrt.2.¹Synthesis and Antiinflamm...", J. Med. Chem., 1974, vol. 17. No. 5, pp. 497-501.

Christen, Vogtle, "Organische Chemie II" 1990, Otto Salle Verlag, Frankfurt.

Abstract of EP 103,544. Mar. 1984.

Dieck, H.A. et al, J. Am. Chem. Soc. 1974, 96(4), pp. 1133-1136.

Ben-David, Y. et al. Organometallics, 1992, 11, pp. 1995-1996.

*Primary Examiner*—C. Warren Ivy
*Assistant Examiner*—Garth M. Dahlen
*Attorney, Agent, or Firm*—Millen, White, Zelano & Branigan

[57] ABSTRACT

A process for preparing substituted 4-methylidenecinnamic acid derivatives of Formula (I).

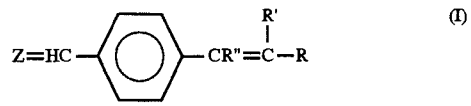

The variables are defined herein. The compounds of Formula (I) can be used, for example, as UV absorbers.

16 Claims, No Drawings

PROCESS FOR PREPARING SUBSTITUTED 4-METHYLIDENECINNAMIC ACID DERIVATIVES

The present invention relates to a process for preparing substituted 4-methylidenecinnamic acid derivatives of the formula (I)

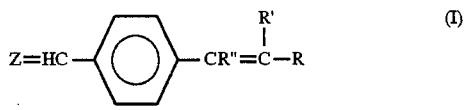

where
R is CN or $COR^1$ where $R^1$ is OH, $O$—$C_6$-$C_{10}$—aryl, $O$—$C_1$-$C_{20}$—alkyl, $NH_2$, $NH$—$C_6$-$C_{10}$—aryl, $NH$—$C_1$-$C_{20}$—alkyl, $N(C_1$-$C_{20}$—alkyl)($C_6$-$C_{10}$—aryl) or $N$—di—$C_1$-$C_{20}$—alkyl,
R' is H, $C_1$-$C_{20}$—alkyl or R,
R" is H, $C_1$-$C_{20}$—alkyl, $C_6$-$C_{20}$—aryl or a radical of the formula

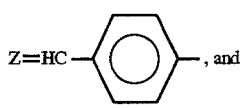

Z is a radical selected from among the formulae II, III and IV

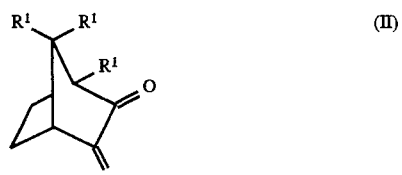

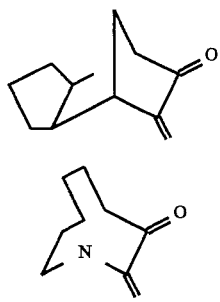

where $R^1$ is H or methyl, characterized in that an aryl halide of the formula (V),

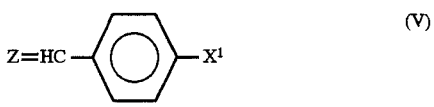

where Z is as defined above and
$X^1$ is Cl, Br or iodine, is reacted with an acrylic acid derivative of the formula (VI),

where R, R' and R" are as defined above, in the presence of palladium catalysts.

BACKGROUND OF THE INVENTION

It is already known that olefins can be arylated by bromoaromatics in the presence of palladium catalysts, phosphine ligands and a base (see R. F. Heck, Org. React. 27, 345–391 (1982)).

Furthermore, for example, EP 0 078 768 and EP 0 103 544 describe Heck couplings between 4-substituted aryl halides and acrylic acid derivatives.

However, these references give no indication that this process can also be used for aryl halides which have an alkenyl group possibly capable of a Heck coupling in the 4-position relative to the halogen atom.

DE 34 45 365 describes the preparation of the compounds of the formula I in which Z is a group of the formula II in a complicated 4-stage process starting from 4'-ethylbenzylidenecamphor, which additionally includes two Wittig reaction steps.

There is therefore a need for a process by means of which the compounds of the formula I can be prepared in fewer process steps, in high space-time yields and using no auxiliaries requiring particular outlay.

SUMMARY OF THE INVENTION

A process has now been found for preparing substituted 4-methylidenecinnamic acid derivatives of the formula (I)

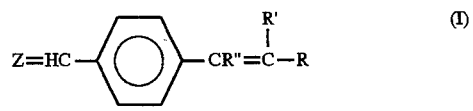

where
R is CN or $COR^1$, where $R^1$ is OH, $O$—$C_6$-$C_{10}$—aryl, $O$—$C_1$-$C_{20}$—alkyl, $NH_2$, $NH$—$C_6$-$C_{10}$—aryl, $NH$—$C_1$-$C_{20}$—alkyl, $N(C_1$-$C_{20}$—alkyl)($C_6$-$C_{10}$—aryl) or $N$—di—$C_1$-$C_{20}$—alkyl,
R' is H, $C_1$-$C_{20}$—alkyl or R,
R" is H, $C_1$-$C_{20}$—alkyl, $C_6$-$C_{20}$—aryl or a radical of the formula

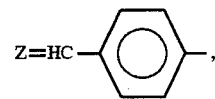

Z is a radical selected from among the formulae II, III and IV

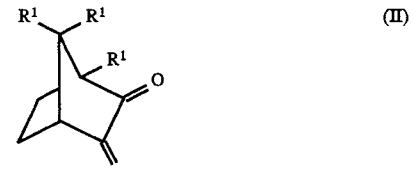

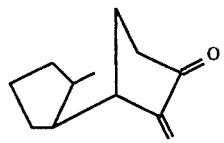

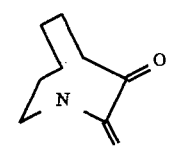

where $R^1$ is H or methyl, which is characterized in that an aryl halide of the formula (V),

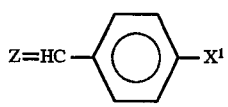

(V)

where Z is as defined above and
$X^1$ is Cl, Br or iodine, is reacted with an acrylic acid derivative of the formula (VI),

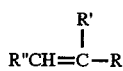

(VI)

where R, R' and R" are as defined above, in the presence of palladium catalysts.

Preferred embodiments are:
a) A process wherein the palladium catalysts used are homogeneous palladium catalysts of the oxidation state 0 and/or +2 in amounts of from 0.0001 to 1 mol of palladium based on aryl halide of the formula (V) used.
b) A process wherein the molar ratio of aryl halide of the formula (V) to acrylic acid derivative of the formula (VI) is in the range from 1:07 to 1:3.
c) A process wherein the aryl halide of the formula (V) is prepared by reacting a compound which corresponds to the aryl halide of the formula (V) but in which Z is O with camphor, norcamphor, 8-ketotricyclo-[5.2.1.0$^{2,6}$]decane or quinuclidinone in the presence of a base or a Lewis acid.

Some of the compounds of the formula I are known (Z=formula II) from DE 34 45 365 and some are new. The novel compounds of the formula I in which Z is a radical selected from among the formulae III and IV and the novel compounds in which R" is a radical of the formula

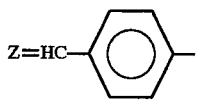

are likewise subject matter of the invention.

Some of the compounds of the formula V are known are some are novel. The compounds of the formula V in which Z is a radical selected from among the formulae III and IV are novel and therefore, also are subject matter of the invention.

The meanings of the radicals R, R' and R" are not critical for carrying out the process of the invention. In the compounds of the formulae I and VI, R is preferably CN or CO—O—$C_1$-$C_{20}$—alkyl, in particular CO—O—$C_1$-$C_{10}$—alkyl.

In the compounds of the formulae I and VI, R' is preferably H or $C_1$-$C_6$—alkyl or has one of the preferred meanings of R. Particularly preferably, R' is H or $CH_3$.

In the compounds of the formulae I and VI, R" is preferably H, $C_1$-$C_6$—alkyl or $C_6$-$C_{10}$—aryl.

The term $C_6$-$C_{20}$—aryl includes carbocyclic and heteroaromatic radicals, in particular unsubstituted and substituted phenyl or naphthalene radicals, preferably the substituents when present are 1 to 5 $C_1$-$C_6$—alkyl or alkoxy groups. It is also possible for one or more CH groups to be replaced by N in the ring to provide, for example, pyridyl, pyrimidyl or pyridazyl groups.

The term "alkyl" herein includes saturated, linear or branched acyclic hydrocarbon groups.

The molar ratio of aryl halide to acrylic acid derivative can be selected as desired. It is preferable to use a molar ratio of aryl halide to acrylic acid derivative of from about 1:0.7–1:3. This ratio is particularly preferably from about 1:0.8–1:1.5.

In a preferred process for preparing the compounds of the formula I in which R" is a radical of the formula

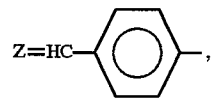

the aryl halide of the formula V is reacted with an acrylic acid derivative of the formula VI in which R" is H, in a molar ratio of from 1:0.3–1:0.6, such that two moles of aryl halide are reacted with the acrylic acid derivative.

The reaction of the invention is preferably carried out in the presence of a base, in particular of an inorganic base. For example, the aryl halide, acrylic acid derivative, the base and, optionally, a solvent may be initially charged and then a palladium salt and phosphine added to form the catalyst.

Suitable inorganic bases for the process of the invention are, for example, alkali metal and alkaline earth metal salts of weak acids, preferably alkali metal and alkaline earth metal hydrogencarbonates and/or carbonates. Particular preference is given to using sodium carbonate. The ratio of aryl halide to base is preferably selected in such a way that from about 0.3–2, particularly preferably from about 0.4–1.3, equivalents of base are used per mol of aryl halide.

The preferred homogenous palladium catalysts generally contain phosphine ligands, particularly Pd(II) with phosphine ligands. Phosphine ligands are commercially available or can be prepared by methods similar to processes known per se.

In the preferred monodentate phosphine ligands of the formula $P(R^2)_3$, the radicals $R^2$ are preferably identical and have a branched alkyl or alkoxy group or a cyclohexyl group or an aryl, in particular phenyl or o-tolyl, group.

Preferred monodentate phosphine ligands are accordingly: trimethylphosphine, triethylphosphine, tripropylphosphine, triisopropylphosphine, tributylphosphine, tricyclohexylphosphine, trimethyl phosphite, triethyl phosphite, tripropyl phosphite, triisopropyl phosphite, tributyl phosphite and tricyclohexyl phosphite, in particular triphenylphosphine, tri(o-tolyl) phosphine, triisopropylphosphine or tricyclohexylphosphine.

Preferred bidentate phosphine ligands are of the formula $(R^2)_2P$—$(R^3)$—$P(R^2)_2$ wherein the $R^2$ groups are independently straight chain or branched $C_1$-$C_6$ alkyl or $C_4$-$C_7$—cycloalkyl and $R^3$ is divalent $C_2$-$C_6$—alkylene, preferably the radicals $R^2$ are each identical and $R^3$ is preferably divalent $C_{2-6}$—alkylene.

Preferred bidentate phosphine ligands are accordingly: 1,2-bis(dimethylphosphino)ethane, 1,2-bis (diethylphosphino)ethane, 1,2-bis(dipropylphosphino) ethane, 1,2-bis(diisopropylphosphino)ethane, 1,2-bis (dibutyl-phosphino)ethane, 1,2-bis(dicyclohexylphosphino) ethane, 1,3-bis(dicyclohexylphosphino)propane, 1,3-bis (diiso-propylphosphino)propane, 1,4-bis (diisopropylphosphino)-butane and 2,4-bis (dicyclohexylphosphino)pentane.

Phosphines can be used in the process of the invention, for example, in a palladium:phosphorus molar ratio of from about 1:0.8–1:2.5. This ratio is preferably from about 1:0.9–1:2.3, particularly preferably about 1:2.

It is self-evident that the ratios indicated are based on the monodentate phosphines of the formula I; for the bidentate phosphines, palladium:phosphine ratios of from about 1:0.4–1:1.25 are generally used.

In a particularly preferred embodiment, it is also possible to use homogeneous palladium catalysts which contain mixed ligands, i.e. both monodentate and bidentate phosphines.

The homogeneous palladium catalysts may be obtained in situ from palladium acetate or palladium chloride and the phosphine corresponding to the ligands.

The process of the invention can be carried out, for example, at temperatures of from about 50°–180° C. Preferred temperatures are from 80°–150° C., particularly preferably in the region of the boiling point of the solvent used. The process of the invention is usually carried out at atmospheric pressure. However, it can also be carried out at subatmospheric or superatmospheric pressure. The use of superatmospheric pressure is appropriate, in particular, if it is desired to work at a reaction temperature at which the individual components of the reaction mixture boil at atmospheric pressure.

The process of the invention is generally carried out under a protective gas, e.g. nitrogen, and with stirring.

The reaction may optionally be conducted in the presence of a solvent and suitable solvents include hydrocarbons, for example toluene, ethers such as tetra-hydrofuran, and polar, aprotic solvents, for example N-methylpyrrolidone (NMP), N,N-dimethylformamide, acetonitrile or dimethyl sulfoxide.

After carrying out the process of the invention, the inorganic salts formed can be separated off, for example, by simple filtration or filtration with suction. It is also possible to allow the salts to settle and to decant off the remaining reaction mixture.

One possible embodiment of the process of the invention is illustrated below by the example of the reaction of 4'-chlorobenzylidenecamphor with 2-ethylhexyl acrylate: 4'-chlorobenzylidenecamphor, 2-ethylhexyl acrylate, sodium carbonate and N-methylpyrrolidone (NMP) are initially charged. Trialkylphosphine and palladium(II) chloride are added in a palladium:phosphorus molar ratio of 1:2. The order of addition of these components can be changed as desired. The mixture is then heated to from 140° to 150° C. under nitrogen and with vigorous stirring. When it has been established that 4'-chlorobenzylidene-camphor is no longer being reacted, the reaction is stopped, i.e. cooled to room temperature and poured into water. The aqueous phase is then separated off and extracted with an organic solvent (e.g. methyl tert-butyl ether (MTB)). The combined extracts obtained are freed of solvent and distilled in vacuo.

In a particularly preferred embodiment, the process of the invention is carried out in the presence of phase-transfer catalysts, e.g. tetraalkylammonium salts, in particular tetrabutylammonium chloride (T. Jeffery, J. Chem. Soc., Chem. Commun. 1287–1289 1984).

It is surprising that the palladium-catalyzed reaction of the invention of 4-methylidenehalobenzenes containing olefinic groups capable of Heck coupling can be reacted in a Heck coupling with acrylic acid derivatives without yield-reducing side-reactions occurring. A further advantage is that the compound of the formula I can be prepared in high space-time yields.

The process of the invention makes possible the preparation of compounds of the formula I under advantageous reaction conditions, with no particular outlay being required for the handling of auxiliaries (bases, solvents). The bases, solvents and phosphines required are readily available and inexpensive.

In comparison with the processes of the prior art, the process of the invention is substantially more economic and achieves a higher space-time yield.

The compounds of the formula I can be used, for example, as UVabsorbers in cosmetics (see DE 34 35 365).

Without further elaboration, it is believed that skilled in the art can, using the preceding description., utilize the present invention to its fullest extent. The following preferred specific embodiments are, therefore, to construed as merely illustrative, and not limitative of the remainder of the disclosure in any way whatsoever.

In the foregoing and in the following examples, temperatures are set forth uncorrected in degrees Celsius and, unless otherwise indicated, all parts and percentages by weight.

The entire disclosure of all applications, patents publications, cited above and below, and of corresponding German application No. P 44 24 489.4, filed Jul. 12, 1994, are hereby incorporated by reference.

EXAMPLE 1

Preparation of a compound of the formula I in which Z=formula II, $R^1$=$CH_3$, R'=H and R=—CO—O—$CH_2$—CH($C_2H_5$)—$C_4H_9$

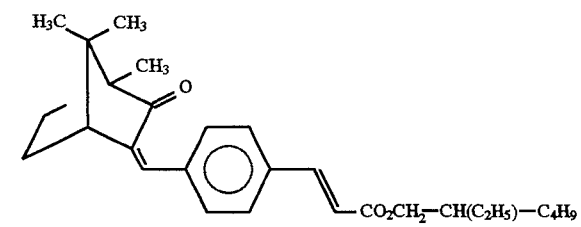

54.8 g of 4'-chlorobenzylidenecamphor, 52.3 g of 2-ethylhexyl acrylate, 10.6 g of sodium carbonate and 200 ml of NMP were placed in a four-neck round-bottom flask and admixed with 2.3 mg of tricyclohexylphosphine and 0.9 mg of palladium acetate (2.0 mol % based on chlorobenzylidenecamphor). The mixture was heated to 140°–150° C. under nitrogen while stirring. After 60 hours, the conversion according to gas chromatography was 68%, based on the 4'-chlorobenzylidenecamphor used.

The mixture is cooled and poured into water. After extraction with 3×200 ml of MTB ether, the combined organic phase is washed with water, dried with sodium sulfate and filtered. After removing the solvent, the residue is distilled under reduced pressure. The yield of isolated product is 48 g.

The following are prepared by a similar method:

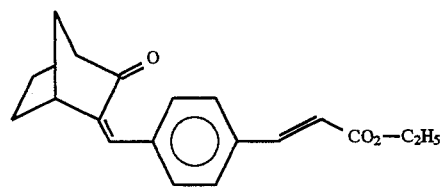

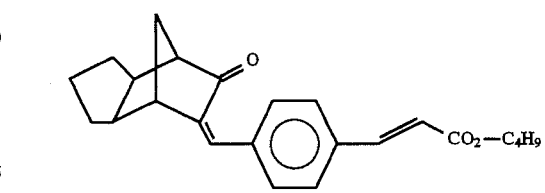

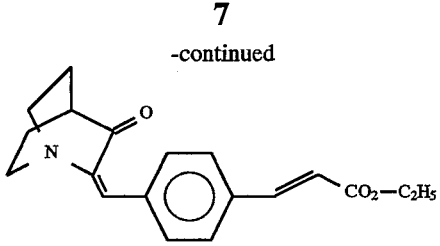

EXAMPLE 2

The procedure of Example 1 was repeated, but adding 1.5 mg of triisopropylphosphine in place of tricyclohexylphosphine. After 60 hours, the conversion according to gas chromatography was 65%, based on 4'-chlorobenzylidenecamphor used.

EXAMPLE 3

The procedure of Example 1 was repeated, but adding triphenylphosphine in place of tricyclohexyl-phosphine and 4'-bromobenzylidenecamphor in place of 4'-chlorobenzylidenecamphor. After 60 hours, the conversion according to gas chromatography was 89%, based on 4'-bromobenzylidenecamphor used.

EXAMPLE 4

The procedure of Example 1 was repeated, but using twice the amount of 4'-chlorobenzylidenecamphor based on 2-ethylhexyl acrylate.

The compound of the formula

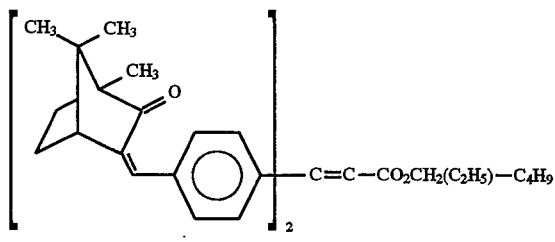

is obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A process for preparing substituted 4-methylidenecinnamic acid compounds of the formula (I)

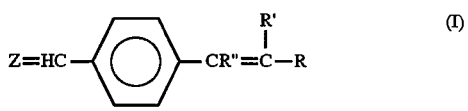

where

R is CN or $COR^1$, where $R^1$ is OH, O—$C_6$-$C_{10}$—aryl, O—$C_1$-$C_{20}$—alkyl, $NH_2$, NH—$C_6$-$C_{10}$—aryl, NH—$C_1$-$C_{20}$—alkyl, N($C_1$-$C_{20}$—alkyl)($C_6$-$C_{10}$—aryl) or N—di—$C_1$-$C_{20}$—alkyl, R' is H, $C_1$-$C_{20}$—alkyl or R, R" is H, $C_1$-$C_{20}$—alkyl, $C_6$-$C_{20}$—aryl or a radical of the formula

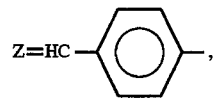

and

Z is a radical selected from among the formulae II, III and IV

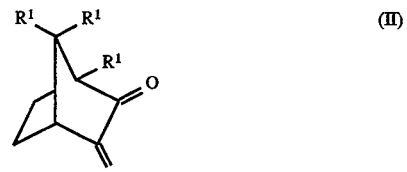

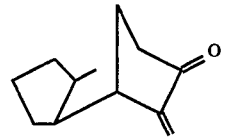

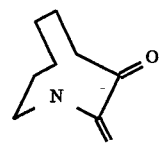

wherein $R^1$ is H or methyl, comprising reacting an aryl halide of the formula (V),

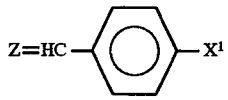

where Z is as defined above and $X^1$ is Cl, Br or iodine, with an acrylic acid of the formula (VI)

where R, R' and R" are as defined above, in the presence of a palladium catalyst and of a phase transfer catalyst.

2. The process according to claim 1, wherein
   the palladium catalyst is a homogeneous palladium catalyst of the oxidation state 0 and/or +2 in an amount of from 0.0001–1 mol % of palladium based on the aryl halide of the formula (V).

3. The process according to claim 1, wherein the molar ratio of aryl halide of the formula (V) to acrylic acid of the formula (VI) is from 1:0.7–1:3.

4. The process according to claim 1, wherein the aryl halide of the formula (V) is prepared by reacting a compound which corresponds to the aryl halide of the formula (V) but in which Z is O with camphor, norcamphor, 8-ketotricyclo[5.2.1.0$^{2,6}$]decane or quinuclidinone in the presence of a base or a Lewis acid.

5. The process of claim 1, wherein R is CN or CO—O—$C_1$-$C_{20}$—alkyl, R' is H, $C_1$-$C_6$—alkyl, CN or CO—O—$C_1$-$C_{20}$—alkyl and R" is H, $C_1$-$C_6$—alkyl or $C_6$-$C_{10}$—aryl.

6. The process of claim 1, wherein in the product of formula I, R" is a radical of the formula

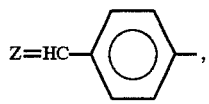

which is prepared by reacting an aryl halide of the formula V with an acrylic acid of the formula VI in which R" is H in a molar ratio of aryl halide to acrylic acid derivative of 1:0.3–1:0.6.

7. The process of claim 1, wherein the palladium catalyst further contains phosphine ligands.

8. The process of claim 1, wherein the reaction is conducted at a temperature of 50°–180° C.

9. The process of claim 1, wherein $X^1$ is Cl, the palladium catalyst is a homogeneous palladium catalyst containing phosphine ligands selected from the formulae $P(R^2)_3$ and $(R^2)_2P-(R^3)-P(R^2)_2$ wherein each $R^2$ is independently a straight-chain or branched $C_1$–$C_6$—alkyl or $C_4$–$C_7$—cycloalkyl and $R^3$ is divalent $C_2$–$C_6$—alkylene and the reaction is conducted in the presence of an inorganic base.

10. The process of claim 1, wherein the palladium catalyst is a homogeneous palladium catalyst formed in situ from a palladium (II) salt and triisopropylphosphine or tricyclohexylphosphine; in the aryl halide of formula V, $X^1$ is Cl, Z is a radical of the formula II and $R^1$ is methyl; in the acrylic acid of formula VI, R' and R" are H and R is —COO—$C_1$–$C_{20}$—alkyl; and, the reaction is conducted in the presence of an inorganic base and an inert solvent.

11. A methylidenecinnamic acid of the formula (I)

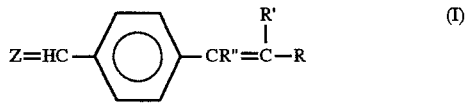

where

R is CN or $COR^1$, where $R^1$ is OH, O—$C_6$-$C_{10}$—aryl, O—$C_1$-$C_{20}$—, alkyl, $NH_2$, NH—$C_6$-$C_{10}$—aryl, NH—$C_1$-$C_{20}$—alkyl, $N(C_1$-$C_{20}$—alkyl)($C_6$-$C_{10}$—aryl or N—di—$C_1$-$C_{20}$—alkyl, R' is H, $C_1$-$C_{20}$—alkyl or R, R" is H, $C_1$-$C_{20}$—alkyl, $C_6$-$C_{20}$—aryl or a radical of the formula

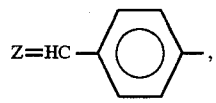

and

Z is a radical selected from among the formulae III and IV

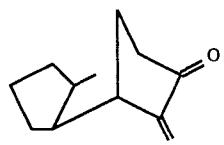

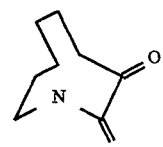

12. Aryl halide of the formula V

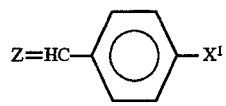

where Z is a radical of the formulae III

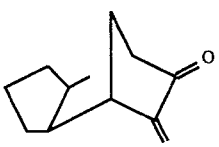

and $X^1$ is Cl, Br or iodine.

13. A methylidenecinnamic acid of the formula I of claim 11, wherein R" is a radical of the formula

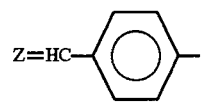

14. The process of claim 1, wherein the phase transfer catalyst is a tetraalkylammonium salt.

15. A process for preparing substituted 4-methylidenecinnamic acid compounds of the formula (I)

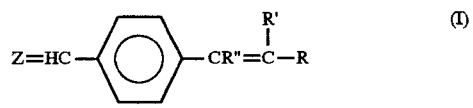

where

R is CN or $COR^1$, where $R^1$ is OH, O—$C_6$-$C_{10}$—aryl, O—$C_1$-$C_{20}$—alkyl, $NH_2$, NH—$C_6$-$C_{10}$—aryl, NH—$C_1$-$C_{20}$—alkyl, $N(C_1$-$C_{20}$—alkyl)($C_6$-$C_{10}$—aryl) or N—di—$C_1$-$C_{20}$—alkyl, R' is H, $C_1$-$C_{20}$—alkyl or R, R" is a radical of the formula

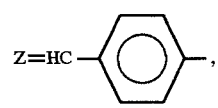

and

Z is a radical selected from among the formulae II, III and IV

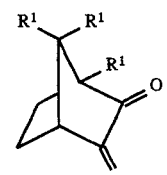

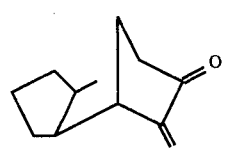

-continued

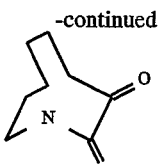
(IV)

wherein $R^1$ is H or methyl, comprising reacting an aryl halide of the formula (V),

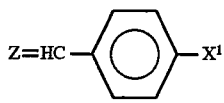
(V)

where Z is as defined above and
$X^1$ is Cl, Br or iodine, with an acrylic acid of the formula (VI)

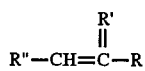
(VI)

where R and R' are as defined above, and R" is hydrogen, in a molar ratio of aryl halide to acrylic acid of 1:0.3 to 1:0.6, in the presence of a palladium catalyst.

16. A process for preparing substituted 4-methylidene-cinnamic acid compounds of the formula (I)

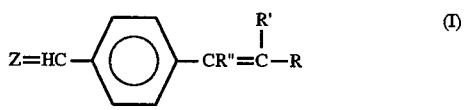
(I)

where
R is CN or $COR^1$, where $R^1$ is OH, O—$C_6$-$C_{10}$—aryl, O—$C_1$-$C_{20}$—alkyl, $NH_2$, NH—$C_6$-$C_{10}$—aryl, NH—$C_1$-$C_{20}$—alkyl, N($C_1$-$C_{20}$—alkyl)($C_6$-$C_{10}$—aryl) or N—di—$C_1$-$C_{20}$—alkyl,
R' is H, $C_1$-$C_{20}$—alkyl or R,
R" is H, $C_1$-$C_{20}$—alkyl, $C_6$-$C_{20}$—aryl or a radical of the formula

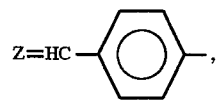

and
Z is a radical selected from among the formulae III and IV

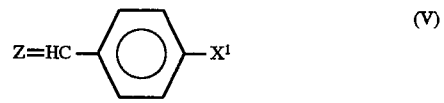
(III)

(IV)

wherein $R^1$ is H or methyl, comprising reacting an aryl halide of the formula (V),

(V)

where Z is as defined above and
$X^1$ is Cl, Br or iodine, with an acrylic acid of the formula (VI)

$$R''-CH=\overset{R'}{\underset{}{C}}-R$$
(VI)

where R, R' and R" are as defined above, in the presence of a palladium catalyst.

* * * * *